United States Patent [19]

Paul

[11] Patent Number: 5,202,438

[45] Date of Patent: Apr. 13, 1993

[54] PROCESS FOR THE SYNTHESIS OF MELAMINE CYANURATE

[75] Inventor: Jean-Michel Paul, Portet/Garonne, France

[73] Assignee: Elf Atochem S.A., La Defense, France

[21] Appl. No.: 863,974

[22] Filed: Apr. 6, 1992

[30] Foreign Application Priority Data

Apr. 4, 1991 [FR] France ............................. 91 04086

[51] Int. Cl.$^5$ .................. C07D 401/12; C07D 251/70
[52] U.S. Cl. ................... 544/198; 544/196; 544/200
[58] Field of Search ..................... 544/196, 198, 200

[56] References Cited

FOREIGN PATENT DOCUMENTS 2030594  4/1980  United Kingdom .

OTHER PUBLICATIONS

Rukevich et al., Chemical Abstracts, vol. 92, Abstract No. 111070s (1980).
Matsuki et al., Chemical Abstracts, vol. 91, Abstract No. 193339c (1979).
Wojtowicz et al., Chemical Abstracts, vol. 97, Abstract No. 91335e (1982).

*Primary Examiner*—John M. Ford
*Attorney, Agent, or Firm*—Millen, White, Zelano & Branigan

[57] ABSTRACT

For the synthesis of melamine cyanurate, by the reaction of cyanuric acid and melamine in an aqueous medium, the reaction is conducted in the presence of a strong mineral acid at a pH not above 1.

20 Claims, No Drawings

PROCESS FOR THE SYNTHESIS OF MELAMINE CYANURATE

BACKGROUND OF THE INVENTION

The present invention relates to a process for the manufacture of melamine cyanurate, in an aqueous medium, from cyanuric acid and melamine and in the presence of a strong mineral acid.

Several methods of synthesis have been proposed in the past for manufacturing melamine cyanurate.

Thus, it is known to manufacture melamine cyanurate by the reaction of cyanuric acid and melamine in an aqueous medium. According to Patent JP 56032470, the reaction is performed at a pH above 7, instead of pH 3 to 12 according to Patent PL 100877.

The synthesis in an aqueous medium may be carried out in the cold state (Patent JP 54055588-A): it is then very slow. A more important prior art relates to processes performed in the heated state. This is the case with Patent JP 55147266-A, which recommends, at the end of the reaction, a removal of water by concentration under vacuum. Similarly, Patent JP 54141792-A relates to a synthesis process at 90° C., according to which the final product is recovered by filtration followed by drying at 105° C.

Moreover, Patent JP 5405587 discloses a process for the manufacture of melamine cyanurate by the reaction of cyanuric acid and melamine in the presence of water in a kneader for 4 hours at 90° C.

Lastly, Patent JP 54125690-A relates to a process for the synthesis of melamine cyanurate by mixing cyanuric acid and melamine in the solid state, followed by heating at 200° C. The latter technique has the drawback of necessitating reactors equipped with powerful means of kneading.

The syntheses in an aqueous medium known hitherto are performed at a pH above 3, and necessitate large amounts of water. In effect, an insufficient dilution leads to the production of pastes, making the use of kneaders obligatory. The removal of such amounts of water at the end of the reaction can become a crippling limitation of these processes, inter alia on account of the excessive time it takes.

Furthermore, the melamine cyanurate obtained by these processes in an aqueous medium has a very fine particle size, so that its filtration by simple means leads to a clogging of the filters unless more complicated filtration techniques, such as tangential filtration, are used. This final product is, in addition, very difficult to wash, and contains impurities, chiefly consisting of unreacted cyanuric acid and melamine.

SUMMARY OF THE INVENTION

An object of this invention is to provide an improved process for the synthesis of melamine cyanurate.

Upon further study of the specification and appended claims, further objects and advantages of this invention will become apparent to those skilled in the art.

To achieve these objects, there is provided a process for the synthesis of melamine cyanurate, by the reaction of cyanuric acid and melamine in an aqueous medium, wherein an improvement comprises conducting the reaction at a pH not above 1, in the presence of a strong mineral acid.

The cyanuric acid/melamine mole ratio is between 0.7 and 1.4, and preferably equal to 1.

At least 70 parts by weight of water, and preferably at least 120 parts by weight of water, are employed per 100 parts by weight of cyanuric acid and melamine.

The [H+]/[melamine] mole ratio is equal to at least 0.5, and preferably between 1 and 1.2.

The reaction may be carried out at a temperature of between 20° and 98° C. at atmospheric pressure.

The synthesis can also be performed under pressure.

Preferably, the reaction is carried out at between 80° and 95° C. at atmospheric pressure for 10 to 30 minutes.

After the reaction, the reaction medium is filtered at a temperature of between 20° and 80° C., and preferably between 50° and 70° C.

The filter cake is then washed copiously with water at a temperature of between 20° and 80° C., and preferably between 50° and 70° C.

Lastly, the cake thus collected is dried in an oven at 120° C. or in a microwave oven.

Any strong mineral acid may be employed. However, hydrochloric acid is preferred, since its use leads to the formation of soluble melamine salts, especially hydrochlorides $-NH_3^+Cl^-$.

The process which is the subject of the present invention eliminates, in effect, at least one if not all of the known drawbacks of the processes in an aqueous medium.

The process which is the subject of the present invention eliminates, in effect, all the known drawbacks of the processes in an aqueous medium.

The medium is not thick, even at a high concentration of cyanuric acid and melamine; stirring is very easy, and the reaction may be performed in a simple stirred reactor.

The use of small amounts of water is permissible. As a result, emptying of the reactor is faster.

Filtration of the melamine cyanurate is easy, even by the simplest means. The final product consists, in effect, of larger particles than those obtained by the known processes. Their particle size distribution conforms to a Gaussian curve centred around 12 microns.

The product collected by filtration can be washed very readily, and freed from its impurities such as residual cyanuric acid or melamine. This process proves to be highly flexible; it makes it possible to work with an excess of cyanuric acid or of melamine, which will be removed on washing.

The purity of the melamine cyanurate obtained is greater than 99.7% by weight.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding French application 9104086, are hereby incorporated by reference.

EXAMPLES

Example 1

Water and then 0.5 mol of hydrochloric acid are introduced successively into a mechanically stirred reactor (anchor type stirrer) heated via a jacket. The temperature of the reaction medium is then brought to 75° C., and 0.5 mol of cyanuric acid and 0.5 mol of melamine are thereafter introduced with stirring.

For each test, the following amounts of water were employed:

| Test No. | Amount of water (g) |
| --- | --- |
| 1 | 500 |
| 2 | 392 |
| 3 | 209 |
| 4 | 187.5 |

The mixture is left stirring for 15 minutes at a temperature of between 80° and 90° C.

The reaction mixture is then cooled to 50° C., filtered through a No. 3 sinter and then washed with water at 50° C.

The final product is dried in an oven at 120° C.

| Test No. | $\frac{CA + Mel}{water} \times 100$ (%) | Appearance of the medium at the end of the reaction | Analysis of the MCA (CA + Mel) by TGA % | HPLC % CA | HPLC % Mel | Cl⁻ ppm | Yield $\frac{MCA\ produced}{MCA\ theoretical}$ (%) |
| --- | --- | --- | --- | --- | --- | --- | --- |
| 1 | 25.5 | very fluid | <0.5 | 0.10 | 0.11 | <10 | 97.7 |
| 2 | 32.5 | very fluid | <0.5 | 0.15 | 0.10 | <10 | 98.0 |
| 3 | 61 | fluid | <0.5 | 0.15 | 0.08 | <10 | 96.7 |
| 4 | 68 | fluid | <0.5 | 0.15 | 0.15 | <10 | 97.5 |

CA: Cyanuric acid;
Mel: Melamine;
MCA: Melamine cyanurate
TGA: Thermogravimetric analysis

Example 2

Examples 2 to 7 are carried out employing 500 g water.

Example 1 is repeated, neutralising the reaction medium with sodium hydroxide before filtration/washing.

A dry product is obtained, the purity of which is good but which contains a little ammeline.

| | No neutralization before filtration HPLC analysis (%) Test No. 4 | Neutralization before filtration HPLC analysis (%) Test No. 5 |
| --- | --- | --- |
| CA | 0.10 | 0.12 |
| Mel | 0.10 | 0.15 |
| Ade | <0.01 | <0.01 |
| Ane | <0.01 | 0.35 |

Ade: Ammelide;
Ane: Ammeline

Example 3

The HCl/melamine mole ratio is varied. The other conditions are those of Example No. 1.

| Test No. | [HCl]/[Mel] | Appearance of the final product | Yield (%) | Analyses TGA (%) | Analyses HPLC (%) |
| --- | --- | --- | --- | --- | --- |
| 6 | 0.1 | hard | 88.4 | CA = 12<br>Mel = 1 | |
| 7 | 0.5 | hard | 85 | CA = 17<br>Mel = 3 | |
| 8 | 1 | very friable | 97 | CA + Mel<br><0.5 | CA = 0.10<br>Mel = 0.10 |
| 9 | 1.1 | very friable | 97.2 | CA + Mel<br><0.5 | CA = 0.11<br>Mel = 0.12 |
| 10 | 1.5 | very friable | 97 | CA + Mel<br><0.5 | CA = 0.12<br>Mel = 0.15 |

Example 4

A test is reproduced under the conditions described in Example 1. For the following tests, numbered n, the HCl-rich filtration liquors originating from test No. (n−1) are used, and these are supplemented with pure HCl in order to adjust the [HCl]/[Mel] mole ratio to a value of 1.

| Test No. | Amount of HCl recovered in the filtrate Moles | Extent of recovery of HCl (%) | Yield (%) MCA | TGA (%) (CA + Mel) | Analyses of the dry product HPLC (%) | Cl⁻ ppm |
| --- | --- | --- | --- | --- | --- | --- |
| 11 | 0.47 | 78 | 96 | <0.5 | CA = 0.16<br>Mel = 0.12 | <10 |
| 12 | 0.40 | 67 | 97 | <0.5 | CA = 0.18<br>Mel = 0.16 | <10 |
| 13 | 0.40 | 67 | 97 | <0.5 | CA = 0.18<br>Mel = 0.20 | |
| 14 | 0.44 | 67.6 | 97 | <0.5 | CA = 0.19<br>Mel = 0.13 | |
| 15 | 0.46 | 75 | 97 | <0.5 | CA = 0.10<br>Mel = 0.10 | |

Example 5

Example 1 is reproduced, varying the filtration temperatures.

| Filtration temperature Test No. | 50° C. 16 Yield MCA % | 50° C. 16 HPLC % | 60° C. 17 Yield MCA % | 60° C. 17 HPLC % | 70° C. 18 Yield MCA % | 70° C. 18 HPLC % |
| --- | --- | --- | --- | --- | --- | --- |
| | 96.7 | CA = 0.16 | 96.6 | CA = 0.20 | 96.4 | CA < 0.02 |

-continued

| Filtration temperature Test No. | 50° C. 16 | | 60° C. 17 | | 70° C. 18 | |
| --- | --- | --- | --- | --- | --- | --- |
| | Yield MCA % | HPLC % | Yield MCA % | HPLC % | Yield MCA % | HPLC % |
| | | Mel = 0.12 | | Mel = 0.14 | | Mel < 0.04 |

Example 6

The synthesis of melamine cyanurate is carried out repeating the conditions of Example 1, except that an excess of melamine is introduced into the reactor, and then an excess of cyanuric acid.

| Test No. | [Mel]/[CA] mole ratio | Composition of the filtration liquors (grams) | | | | Yield MCA % | Analyses of the MCA % | |
| --- | --- | --- | --- | --- | --- | --- | --- | --- |
| | | Mel | CA | Ade | Ane | | HPLC (%) | Cl⁻ ppm |
| 19 | 1.1 | 4 | 2.7 | 0.9 | 0 | 98.8 | CA = 0.13 Mel = 0.13 | 20 |
| 20 | 0.90 | 1.1 | 5.0 | 0.12 | 0.37 | 97 | CA = 0.10 Mel = 0.14 | 10 |

This example shows that the excess of one of the two starting reactants is carried away in the filtration liquors.

Moreover, the laser particle size distribution of the melamine cyanurate takes the form of a Gaussian curve centered around 12 microns.

Example 7

Example 1 is repeated, replacing HCl with $H_2SO_4$. The reaction medium is thicker.

HPLC analysis of the melamine cyanurate shows the following percentages:
CA=0.07%
Mel=0.16%
Ane=90 ppm
$SO_4^{2-}$=900 ppm Sulphate ions appear to be more difficult to extract from melamine cyanurate by washing than chloride ions.

Example 8

The reaction is performed in a mechanically stirred 1 m³ enamelled reactor. Heating of the reactor is effected with steam under a pressure of 3 bars. 800 l of water are charged, followed by 89.7 kg of HCl at a concentration of 36.7% by weight; the mixture is heated to 75° C., and 100.8 kg of melamine and 103.2 kg of cyanuric acid are then introduced. The mixture is maintained at 90°-93° for 30 minutes; it is then cooled to 50° C. and filtered through a Büchner (polypropylene filter cloth of porosity 2 microns). The cake is washed with 700 l of water at 50° C. and dried in an oven at 120° C.

| Test No. | Appearance of the dry MCA | Yield MCA % | Analyses of the MCA | | |
| --- | --- | --- | --- | --- | --- |
| | | | HPLC % | Cl⁻ ppm | Particle size |
| 22 | white | 96.5 | CA = 0.13 Mel = 0.14 | <10 | centred around 12 microns |

Example 9

The reaction is performed in the same reactor as in the previous example, decreasing the water/(CA+Mel) mass ratio. In effect, 350 kg of water, 64.5 kg of cyanuric acid, 63 kg of melamine and 56 kg of HCl at a concentration of 36.1% by weight are introduced into the reactor.

The reaction is performed at 90°-93° C. for 30 minutes, the filtration at 50° C. and the washing with 700 liters of water at 50° C.

| Test No. | % yield MCA | Analysis of the MCA | | |
| --- | --- | --- | --- | --- |
| | | HPLC % | Cl⁻ ppm | Particle size |
| 23 | 95 | CA = 0.11 Mel = 0.12 | <10 | centred around 12 microns |

In this example, the productivity has been increased by decreasing the reaction volume and the amount of water. A small decrease in yield is observed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the synthesis of melamine cyanurate, by the reaction of cyanuric acid and melamine in an aqueous medium, the improvement which comprises conducting the reaction at a pH not above 1, in the presence of a strong mineral acid.

2. A process according to claim 1, wherein the cyanuric acid/melamine mole ratio is between 0.7 and 1.4.

3. A process according to claim 2, wherein the cyanuric acid/melamine mole ratio is equal to 1.

4. A process according to claim 2, wherein at least 70 parts by weight of water are employed per 100 parts by weight of cyanuric acid and melamine.

5. A process according to claim 4, wherein at least 120 parts by weight of water are employed per 100 parts by weight of cyanuric acid and melamine.

6. A process according to claim 4, wherein the [H+]/[melamine] mole ratio is equal to at least 0.5.

7. A process according to claim 6, wherein the [H+]/[melamine] mole ratio is between 1 and 1.2.

8. A process according to claim 6, wherein the reaction is carried out at a temperature of between 20° and 98° C.

9. A process according to claim 8, wherein the reaction is carried out at a temperature of between 80° and 95° C. for 10 to 30 minutes.

10. A process according to claim 6, wherein the synthesis is performed at a pressure above atmospheric pressure.

11. A process according to claim 8, wherein, after the reaction, the reaction medium is filtered at a temperature of between 20° and 80° C.

12. A process according to claim 11, wherein, after the reaction, the reaction medium is filtered at a temperature of between 50° and 70° C.

13. A process according to claim 11, wherein the filter cake is washed with water at a temperature of between 20° and 80° C.

14. A process according to claim 13, wherein the temperature of the washing water is between 50° and 70° C.

15. A process according to claim 13, wherein the filter cake is finally dried in an oven at 120° C. or in a microwave oven.

16. A process according to claim 15, wherein the strong mineral acid is hydrochloric acid.

17. A process according to claim 12, wherein the process is conducted at atmospheric pressure.

18. A process according to claim 1, wherein the strong mineral acid is hydrochloric acid.

19. A process according to claim 18, wherein at least 120 parts by weight of water are employed per 100 parts by weight of cyanuric acid and melamine.

20. A process according to claim 19, wherein the reaction is carried out at a temperature of between 80° and 95° C. for 10–30 minutes.

* * * * *